United States Patent

Hall et al.

Patent Number: 5,493,038
Date of Patent: Feb. 20, 1996

[54] METHOD OF PREPRATION OF LITHIUM ALKYLAMIDES

[75] Inventors: Randy W. Hall, Kings Mountain; Conrad W. Kamienski; Robert C. Morrison, both of Gastonia; John F. Engel, Belmont, all of N.C.

[73] Assignee: FMC Corporation, Philadelphia, Pa.

[21] Appl. No.: 204,724

[22] Filed: Mar. 2, 1994

[51] Int. Cl.$^6$ .................................................. C07F 7/10
[52] U.S. Cl. .................... 556/412; 556/463; 556/466; 564/2; 564/463; 252/182.12
[58] Field of Search ................. 564/2, 463; 556/412, 556/466; 252/182.12

[56] References Cited

U.S. PATENT DOCUMENTS

| | | | |
|---|---|---|---|
| 4,206,191 | 6/1980 | Morrison | 423/413 |
| 4,595,779 | 6/1986 | Morrison | 564/2 |
| 5,002,689 | 3/1991 | Mehta | 252/182.12 |
| 5,321,148 | 6/1994 | Schwindeman | 556/466 |

*Primary Examiner*—Paul F. Shaver
*Attorney, Agent, or Firm*—Charles C. Fellows; Robert L. Anderson

[57] ABSTRACT

A process for quickly preparing easily separable solutions of lithium alkylamides, as exemplified by the formula $$(R_3M)_xNLi(R1)_y \cdot (LB)_z \qquad (I)$$

wherein M is silicon or carbon, R and $R^1$ are $C_1$–$C_8$ alkyl, cycloalkyl or alkylene groups, LB is a Lewis base, x and y are integers equaling 2, and z is greater than 1, comprising the steps of reacting lithium metal in bulk form with an alkylamine in mole ratios of metal to alkylamine ranging from 2 to 1 to 10 to 1 in a solvent selected from ethereal or selected from the group consisting of conjugated dienes, vinyl aromatic and polycyclic aromatic compounds, under an inert atmosphere at elevated temperatures for 1 to 10 hours, cooling the product and separating the product solution from the unreacted lithium metal in the reactor.

10 Claims, No Drawings

METHOD OF PREPRATION OF LITHIUM ALKYLAMIDES

This invention concerns a process for preparing lithium alkylamides by reacting lithium metal in gross or bulk form with an alkyl amine.

Lithium alkylamides of the formula $(R_3M)_xNLi(R^1)_y.(LB)_z$ where M=Si or C, LB=Lewis Base, R and $R^1$ are alkyl, cycloalkyl, and alkylene groups containing 1 to 8 carbon atoms, x+y=2, z< 1. Examples are lithium hexamethyldisilazide and lithium diisopropylamide. $R_3M$ & $R^1$ may be combined (where M=C) to give a divalent alkylene radical, yielding a cyclic alkylamide where R & $R^1$ taken together may contain 4 to 8 carbon atoms such as the N-lithio salts of pyrrolidine and hexamethyleneimine. Lithium alkylamides are used in the preparation of pharmaceutical intermediates and in general organic synthesis. In U.S. application Ser. No. 129,818 filed Sep. 30, 1994, there is described a process for preparing clear, suspensoid-free solutions of lithium tert-butoxide in ethereal or hydrocarbon solvents by reaction of lithium metal in gross or bulk form with a limiting quantity of tert-butyl alcohol. In U.S. Pat. Nos. 5,002,689 and 4,595,779 are described methods for producing lithium dialkylamides in ether or in mixed ether-hydrocarbon solvents using lithium metal in a finely dispersed state.

Although lithium metal in a finely dispersed state reacts rapidly with alkylamines in mixed THF-hydrocarbon media in the presence of an electron carrier such as styrene, such lithium dispersions are costly to produce, requiring the steps of (a) heating of bulk lithium metal and mineral oil to about 190°–200° C. in the presence of a dispersion aid, such as oleic acid, (b) stirring the resultant molten mixture at high speeds in a special dispersion unit to produce the required small particle sizes (generally less than 100 microns), then (c) cooling the product (preferably without stirring), and then finally (d) removing the mineral oil from the solidified lithium metal particles by washing several times with a volatile hydrocarbon solvent, such as hexane or pentane. The volatile hydrocarbon solvent can optionally be removed by purging with an inert gas such as argon, or more preferably, be washed one or more times with the reaction solvent before reaction with the alkylamine.

Besides being costly to produce, lithium dispersion also may add undesirable impurities, such as, e.g., mineral oil and oleic acid breakdown products, and volatile hydrocarbons to the subsequent lithium alkylamide product dissolved in THF or mixed THF-hydrocarbon solvent media.

Because of the extremely small sizes of the lithium metal particles, a high proportion of solid impurities, small in size may also be present after reaction with the alcohol is complete. Impurities on the lithium surface slow down the initial reaction. These impurities arise from side reactions with traces of oxygen in the inert atmosphere, of traces of water in the solvent and alkylamine and with the solvent itself. These small solid impurities (including any unreacted lithium metal particles) cause filtration problems, although the use of an excess of the alkylamine generally takes care of any unreacted lithium metal.

The present invention provides a process for quickly preparing in high yield, easily separable solutions of lithium alkylamides in an economically feasible time period of 1 to 10 hours, comprising the steps of reacting lithium metal in bulk form ["Bulk" form is defined herein as lithium metal, as obtained from manufacture in an electrolytic cell, without further remelting in a hydrocarbon oil to effect comminution thereof by means of some form of agitation. The bulk lithium metal may be further reduced in size by an extrusion process and subsequent cutting into smaller, more manageable pieces or even by directly slicing the cell "ingot" into smaller pieces but generally not smaller than 0.5 grams per piece], with an alkylamine in mole ratios of lithium metal to alkylamine ranging from 0.9 to 1 to 10 to 1 in an ethereal or mixed ethereal/hydrocarbon solvent under an inert atmosphere at elevated temperature in the presence of an electron carrier selected from the group consisting of conjugated dienes, vinyl aromatic and polycyclic aromatic compounds, cooling the product and separating the product from the unreacted lithium metal in the reactor; the process is conveniently continued by adding additional solvent, sufficient lithium metal and alkylamine to the unreacted metal in the reactor to maintain the mole ratio of lithium metal to alkylamine, and continuing the reaction, thereby to form further lithium alkylamide, and repeating said steps a number of times.

Unexpectedly, the process of the present invention overcomes problems experienced with the use of lithium metal in a finely divided (dispersed) state without experiencing a great increase in reaction time by the use of a sufficient excess of lithium metal in bulk form (over and above the alkylamine used). Impurities on the lithium surface slow down the initial reaction. Surprisingly, the amount of lithium metal in bulk form needed to preserve a comparable overall reaction time when compared to lithium in dispersed form is only in the order of about two to three times.

For example, the surface area of one gram equivalent of lithium metal particles 20 microns in diameter is about 13,000 square centimeters, while the surface area of an equivalent amount of lithium metal cubes with dimensions of one centimeter by one centimeter by one centimeter is only 79 square centimeters, a one hundred sixty-six times greater surface area for the dispersed lithium. One would therefore expect the relative amount of lithium in bulk form needed to give a overall reaction rate comparable to the dispersed lithium to be in the order of one hundred sixty-six times greater. Instead, only about two to three equivalents of lithium metal in the form of ½ inch by ½ inch rods was found to react with one equivalent of alkylamine in a comparable overall reaction time (2–3 hours) as did one equivalent of lithium metal dispersed to 20 micron diameter particles (about 1–2 hours) See the Table.

After the reaction of one of the 2–3 equivalents of the bulk lithium metal is completed, the slightly hazy product solution can be easily decanted from the unreacted floating metal and filtered quickly. Another reaction can be started in the same reactor, adding only another equivalent each of lithium metal and alkylamine, half an equivalent of styrene and the required amount of solvent. When the process is to be repeated one or more times in the same reactor it is advantageous but not necessary to immediately add additional solvent after the product of the preceding reaction is recovered. However, preconditioning of the lithium metal does not appear to be a problem in proceeding from the first run to the second or succeeding runs. The lithium metal becomes completely shiny following initiation of the reaction and overall reaction times for these runs are about the same, depending on reaction temperature.

The ease of separation of the product solution from unreacted lithium metal is maintained in each subsequent run and there is no hazardous unreacted lithium to be disposed of as in the runs using dispersed lithium.

There does not appear to be any dependency of reaction rate on the contained sodium level in the lithium metal used in the reaction with alkylamines as was noted with tertiary alcohol.

It is quite unexpected that the size of the lithium metal pieces used in in the reaction with alkylamines in tetrahydrofuran or tetrahydrofuran-hydrocarbon mixtures can be varied widely, depending on the batch size of the runs, without unduly affecting (reducing) the overall reaction time. Thus, any of the common commercially available sizes of lithium metal may be employed or segments [pieces] may be cut from these.

Sizes of bulk lithium metal available commercially which can be used are: one inch (2.5 cm) diameter by 8 inch (20.3 cm) long rods, one-half inch 1.3 cm) by 6.5 inch (16.5 cm) long rods, 2.25 inch (5.7 cm) by 3.38 inch (8.6 cm) long cylindrical ingots [¼ lb], 3 inch (7.6 cm) diameter by 3.8 inch (9.7 cm) long cylindrical ingots [½ lb (227 g)], 4 inch (10.2 cm) diameter by 5 (12.7 cm) inch long cylindrical ingots [1 lb (454 g)], and two pound (908 g) trapezoidal ingots having dimensions of 2.5/3.5 inches (6.4/8.9 cm) in width by 3.25 inches (8.3 cm) in height by 10.5 inches (26.7 cm) in length. Lithium metal dispersion, 30 weight per cent in mineral oil with 90% of the particles greater than 10 microns, but less than 50 microns, (average: 20 microns) is used for comparison.

The optimum size of the lithium metal employed will depend upon the size of the reaction being carried out. Generally, the size of the pieces of lithium being employed will be such that the overall reaction time will be less than 8–10 hours. The pieces of metal should be easily visible as being discrete particles, i.e., not particles produced by a dispersion process as described above [less than 0.1 millimeter] and should generally weigh at least 0.5 gr per piece.

Generally, it is preferable to use excesses of such bulk metal relative to the alkylamine in the range of 2:1 to 10:1, but, most preferably 3:1 to 5:1

Generally, all the dialkylamine (e.g., diisopropylamine) can be mixed with the bulk metal and hydrocarbon solvent initially and then the styrene dissolved in ethereal solvent (THF) added gradually to carry out the reaction. In the case of the silysubstituted amines, it is preferable to add the amine and electron carrier together. The reaction temperature of the former reaction is kept between 35° and 45° C., while the temperature of the latter reaction may be higher, e.g., at the boiling point of THF.

The reactions may be carried out at ordinary [atmospheric] pressure, but the atmospheric composition above the contents of the reaction vessel should be inert. Thus, the atmosphere should be dry and inert to lithium metal, i.e., most favorably be argon gas. Higher pressures, i.e., those above atmospheric, may be employed to raise the reaction temperature and thus, to further speed up the reaction, but are not required.

The alkylamine reactants which may be used in this process are of the form:

$$(R_3M)_xN(H)(R^1)_y \qquad (I)$$

In formula (I) M is silicon or carbon, R and $R^1$ are alkyl, cycloalkyl and alkylene groups with 1–8 carbon atoms, and x and y are whole numbered integers and x+y equals 2. $R_3M$&$R^1$ may be combined (where M=C) to give a divalent alkylene radical yielding a cyclic alkylamine where R and $R^1$ taken together may contain 4 to 8 carbon atoms.

Thus typical examples of (I) compounds are dialkylamines where x is zero, and y is 2. When y is two the dialkylamine is symmetrical, i.e., having the same alkyl groups. Such dialkylamines can be represented by diisopropylamine, diisobutylamine, and so forth.

When M is silicon and x is one and y is one, the formula (I) compounds are unsymmetrical alkyl, trialkylsilyl amines, such as e.g., t-butyl-trimethylsilylamine. When M is carbon, and x is one and y is one, the formula (I) compounds are unsymmetrical dialkylamines, such as, e.g., methyl-, cyclohexylamine, ethyl-isobutylamine, and so forth.

When M is carbon, and R and $R^1$ are taken together to form an alkylene radical, a cyclic amine is generated in formula (I), e.g., when R and $R^1$ taken together contain 4 carbon atoms, pyrrole is formed, when R and $R^1$ contain 5 carbon atoms, pyrollidine is formed, and when R and $R^1$ contain 6 carbon atoms, hexamethyleneimine is formed.

When x is two and y is zero, the formula (I) compounds are bis-trialkylsilylamines such as hexamethyldisilazane.

Electron "carrier" reaction promoters are conjugated dienes, vinylaromatic compounds, or polycyclic aromatic compounds such as isoprene, styrene or naphthalene. Isoprene and styrene are preferred. Normally these electron "carriers" are the limiting reagents and react first with lithium metal to produce radical ions which then further react with the alkylamine to give the desired lithium alkylamide. Since the "carrier" can generate two such active ionic sites, only half as much "carrier" as alkylamine is required.

Solvents which may be used in the process of this invention to prepare lithium alkylamides are generally ethers and mixtures thereof with hydrocarbon media. Generally, at least one molar equivalent of the ether to be employed must be present for every mole of lithium alkylamide generated, with the remainder being an aliphatic or aromatic hydrocarbon solvent. However, in the case of the lithium dialkylamides, the ratio of the ether tetrahydrofuran to lithium dialkylamide should not exceed two (see U.S. Pat. No. 5,002,689). When M is silicon in (I) above, however, the entire solvent employed may be of the ethereal type. Thus, for example, in the case of the lithium dialkylamide being lithium diisopropylamide, the preferred ether (THF) to amide ratio is 1.1 to 1.9. The rest of the solvent may be an aliphatic hydrocarbon such as hexane, cyclohexane or heptane, or it may be an aromatic solvent such as toluene or ethylbenzene. On the other hand, in the case of the lithium hexamethyldisilazide, the solvent may be either pure THF or a mixture of THF and a hydrocarbon such as cyclohexane.

The ethereal solvents useful in practicing the invention include but are not limited to diethyl ether, dibutylether, methyl-t-butyl ether, tetrahydrofuran, methyltetrahydrofuran, 1,2 dimethoxyethane and the like. The hydrocarbon solvents where used in combination with the above ethereal solvents may comprise aliphatic solvents such as pentane, hexane, and heptane, cycloaliphatic solvents, such as cyclopentane and cyclohexane, and aromatic solvents such as benzene, toluene, ethylbenzene cumene, and mesitylene.

These amides have not previously been made in methytert-butyl ether. Besides being a much less costly solvent than THF, MTBE is a superior solvent for recycling purposes, possessing a low solubility in water and a low boiling point, as well as no tendency to form dangerous peroxides.

The reaction temperatures employed vary with the nature of the lithium alkylamide. This, e.g. it is preferable to maintain the temperature below 50° C. when preparing the more reactive (to THF) lithium diisopropylamide. However, lithium hexamethyldisilazide may be prepared in pure THF at the reflux temperature. Generally, the preferred reaction temperature range in THF is from 50° C. to reflux for lithium hexamethyldisilazide preparations employing bulk lithium metal.

The following examples further illustrate the invention.

Exemplary Run of Lithium Diisopropylamide Employing Bulk Lithium Metal (Solvent=Tetrahydrofuran (THF) and Heptane) (8789)

A volume of 50 ml of heptane (dry) was added to a 500 ml Morton flask, equipped with mechanical stirrer, dropping funnel, cold finger condenser, and thermometer, maintained under an inert argon atmosphere. Additionally, there were added to the flask: 10.22 grams (1.472 moles, 12 pieces), of lithium metal in the form of ½ inch by ½ inch rod (sodium content of lithium metal less than 100 ppm) and 96.9 g (0.9575 m) of diisopropylamine (dry). In the dropping funnel were placed 78.0 g (1.08 moles) of dry tetrahydrofuran, of which 20 ml was added immediately to the reactor contents, and this was followed by 41.8 g (0.401 moles) of styrene, which was the limiting reagent. Thus, assuming a theoretical yield of 0.802 moles of lithium diisopropylamide (LDA), the lithium metal was present in 83.4 mole % excess and the amine in 19.3 mole % excess. The theoretical ratio of THF to LDA was 1.346.

The reaction mix was stirred slowly (212 rpm) and heated to 36.5° C., at which time the styrene/THF feed was begun at a rate of 1–2 drops/second. After about 3 minutes, the reaction started up (haziness appearing in the solution). The remainder of the feed was added in 56 minutes, the internal reaction temperature being maintained between 37° C. and 41° C. by means of an external cooling bath. After stirring for a further 18 minutes (t=40°–42° C.), the reaction was essentially complete (97.4%) as determined by the Watson-Eastham titration method. After filtration (16 minutes), and 2 washes with 25 ml heptane each the concentration of the solution was found to be 29.5 wt % in LDA. A weight of 283.9 g of a yellow solution was obtained. Five to six mole % of dibutylmagnesium (based on LDA content) was added as stabilizer.

Preparation of Lithium Diisopropylamide Employing Bulk Lithium Metal (Solvent=Methyl tert-butyl ether) (8804)

To a reactor equipped as described above and containing 15.18 grams (2.188 moles) lithium metal in form of cut rod pieces (34 pieces, different sizes) was added 59.9 g (0.592 m) of diisopropylamine. To the dropping funnel was added 191.5 g (2.172 moles) of methyl tert-butyl ether, (MTBE) of which 180 ml was drained into the reactor, and 25.9 g (0.2486 m) of styrene. Addition of the MTBE/styrene was begun (in 2 drops/sec) and the reaction initiated in about 9 min (hazy solution). After this the feed was continued with the temperature varying from 40°–55° C. Total feed time was 42 min. Samples were then withdrawn to determine the extent of reaction (post-feed). Results were: t=2 min, 82.9% yield; t=6 min, 88.5%; t=10 min, 89.7%; t=15 min, 91.5%; t=21 min, 92.6%; t=33 min, 92.6%. The concentration of lithium diisopropylamide in solution at this point was 27.1 wt %. The product was stable in the refrigerator at −10° C. Filtration to give a golden solution was rapid (25 ml/min).

Comparative Run of Lithium Diisopropylamide Employing Lithium Dispersion. (8587) (Solvent=THF and Heptane)

A weight of 14.18 g (2.04 m) of lithium metal powder (containing 0.18 wt percent sodium), 55 ml heptane and 158.6 g (1.567 m) of diisopropylamine were added to a reaction flask equipped as described above. To the dropping funnel was added 67.81 g (0.6507 m) of styrene and 133.5 g (1.85 m) of dry THF, of which 84 ml of THF was added to the reactor. The reaction was initiated at 27.2° C. and the feed continued between 34° and 39° C. (total feed time=47 min). After an additional 51 minutes, the reaction mixture was filtered and washed with heptane to give 530 ml of a golden-colored solution. A weight of 79.31 g of a 13.5wt % solution of dibutylmagnesium in heptane was added as stabilizer. The yield of lithium diisopropylamide was 98.2% and the concentration was 2.50 meq/kg of solution or 26.8 wt %..

Exemplary Consecutive Runs of Lithium Hexamethyldisilazide Employing Bulk Lithium Metal. (Solvent=Tetrahydrofuran) Run 8768 See Table for details of Consecutive Runs 1 to 6

A weight of 8.90 g (1.28 m) of lithium metal cut in the form of 1 cm by 1 cm cubes (13 pieces) containing 57 ppm sodium were placed in a 500 ml flask equipped with mechanical stirrer, cold finger condenser, thermocouple and dropping funnel. The metal was quite coated over with a dark (black) coating. A weight of 114 grams (1.58 m) of tetrahydrofuran (13 ppm H2O) was added to the metal. To the dropping funnel was added 21.0 g (0.2015 m) of styrene and 67.8 g, (0.42 m) of hexamethyldisilazane. The reaction could not be initiated even after heating to 51° C.

A weight of 7.49 grams (1.079 m) of lithium metal rod (0.5 in diameter), cut into half inch long pieces (11) containing 0.74% sodium was next added to the reactor. The metal pieces were not coated as above. The feed of styrene and hexamethyldisilazane was continued and the reaction initiated quickly, with the lithium rod pieces becoming quite shiny. The lithium metal cubes did not initiate, remaining quite black. The feed addition took 36 minutes, the temperature being maintained at 44°–46° C. Samples were taken from the reaction periodically to determine the extent of the reaction. After 11 minutes (post-feed) the yield was 90.5%, after 19 minutes, 92%, after 33 minutes, 94.5%, and after 1 hour, remained at 94.5%. The production solution began to precipitate product but, the product and crystals were transferred as completely as possible from the reactor flask. Filtration of the product solution was slow because of product saturation of the solution (pale yellow).

Second Consecutive Run (Run 8772)

After removal of the black metal cubes from the reaction flask above, there were remaining in the flask 4.69 g (0.676 m) of lithium metal in the form of rods (shiny). To these were added an additional 3.49 g (0.5029 m) of rod pieces (black coating on sides, shiny on ends) to give a total of 1.179 moles of metal. Also added was 182 g (2.52 m) of THF. To the dropping funnel was added 26.1 g (0.2505 g) of styrene and 83.1 g (0.5148 m) of hexamethyldisilazane. This mixture was fed to the metal/THF reactor contents at the rate of about 2 drops/sec (initial temp=32.7° C.).

After addition of about 15% of the feed, all the lithium metal pieces became shiny. The reaction temperature rose to 47° C. at the end of the feed. Periodic sample withdrawal and analysis gave the following post-feed results: 4 min, 71.4% conversion; 12 min, 79%; 22 min, 83%; 30 min, 86.5%; 123 min, 91.2%; 166 min, 92%; 188 min, 92.6%; 220 min, 92.0%.

The product solution was pumped away from the remaining lithium metal in the flask and filtered in 8 minutes, using a small amount of filter aid, to give a slightly hazy yellow solution.

Third Consecutive Run (8773)

To the reactor containing the unreacted metal from the second consecutive run was added an additional 3.38 grams (0.487 m) of lithium metal rod pieces. A weight of 182.2 g (2.53 m) of THF was added to the metal in the flask. To the dropping funnel was added a mixture of 24.5 g (0.2351 m) of styrene and 80.4 g (0.4981 m) of hexamethyldisilazane. The solutions was then added at the rate of 2 drops per second to the stirred metal in the flask at an original reaction temperature of 44.5° C. The temperature rose to 72.5° C. at the end of the styrene-hexamethyldisilazane feed and continued on to reflux (77° C.). Samples of the reaction solution were then withdrawn periodically to determine the extent of the reaction. The reaction temperature was kept at reflux during this time. The results were: 83.4% conversion at 6.5 minutes (post-feed); 92.4% at 18.5 minutes; 94.5% at 44 minutes; 94.8% at 67 minutes; 95.1% at 90 minutes and 94.8% at 150 minutes. The product solution was filtered in 8 minutes to give a hazy pale yellow solution.

Fourth Consecutive Run (8776)

To the reactor containing the unreacted metal from the third consecutive run (8773) was added an additional 0.66 g (0.095 m) of lithium metal rod (1 piece) to give a total of 0.791 m of lithium metal. Also added was 182.6 g (2.532 m) of THF. A mixture of 22.0 g (0.2112 m) of styrene and 69.8 g (0.4324 m) of hexamethyldisilazane were placed in the dropping funnel. After heating the reactor contents to 56.8° C., the styrene-hexamethydisilazane mixture was fed to the lithium metal-THF at a rate of about 2 drops per minute. Within 30 seconds the reaction began and the reaction temperature continued to increase to near reflux (72.6° C.) at the end of the feed (total feed time=34 minutes). Samples of the solution were then withdrawn periodically and assayed for lithium hexamethyldisilazide. The results were: 87.7% yield 4 minutes after feed complete; 90.6% yield 24 min after; 94.0% one hour after; 94.1% 1.68 hours after. The product was then cooled, pumped away from the unreacted metal and filtered to give a hazy pale yellow solution.

Fifth Consecutive Run (8780)

To the remaining lithium metal rod (shiny) in the reactor from the fourth consecutive run was added an additional 5.19 g (0.7478 m) of lithium metal rod pieces (6) to give a theoretical metal content of 1.11 moles. Also added to the flask was 177.6 g (2.462 m) of THF. A mixture of 21.0 g (0.2015 m) of styrene and 67.5 g (0.4182 m) of hexamethyldisilazane was placed in the dropping funnel. The reactor contents was heated to 46.2° C. and addition begun at about 2 drops/sec. After about 5 minutes reaction was noted. The remainder of the addition was carried out while keeping the reaction temperature between 35° and 38° C. After the feed was complete (34 minutes), samples of the solution were withdrawn periodically to determine the extent of reaction. One minute after the feed was complete the yield was 63.0% (the reaction temperature was again kept at about 34°–38° C.). Further results were: 71.0% yield after 8 min; 81.0% after 18 min; 85.1% after 39 min; 91.4% after 102 min. The solution was pumped away from the unreacted metal and filtered to give a pale yellow solution.

Sixth Consecutive Run (8781)

To the remaining lithium metal rod (theory=0.697 m) in the reactor from the fifth consecutive run was added an additional 11.14 g (1.605 m) of lithium metal rod pieces (14) and 198.2 g (2.748 m) of THF. A mix of 24.8 g (0.2380 m) of styrene and 85.81 g (0.5319 m) of hexamethyldisilazane was placed in the dropping funnel. The feed was begun at 40.3° C. and the temperature controlled at 37°–41° C. throughout the feed (34 minutes). Analysis of the product solution after the feed was complete indicated the following: 75.0% yield after 1 min; 86.6%, 11 min; 90.4%, 25 min; 93.6%, 86 min. The product solution was pumped off and filtered to give a colorless solution.

Comparative Run of Lithium Hexamethyldisilazide Employing Lithium Dispersion (Solvent=THF) (8356)

A weight of 7.65 g (1.10 m) of lithium metal powder and 148.5 g (2.059 m) of THF were placed in a flask equipped as above. To the dropping funnel were added 20.31 g (0.1949 m) of Styrene and 67.9 g (0.4207 m) of hexamethyldisilazane. The reaction was initiated at 37.7° C. and the temperature controlled at 38°–39° C. during the addition (64 min. feed time). After standing overnight, the mixture was filtered in 6 minutes to give 306.4 g of a 1.2 molar pale yellow solution (quantitative).

Run of Lithium Hexamethyldisilazide Employing Bulk Lithium Metal Solvent-Methyl tert-butyl ether) (8802)

To a reactor containing clean lithium metal pieces, (12.7 g, 1.828 m, 28 pieces) used previously to produce lithium hexamethyldisilazide, was added an additional 5.30 g (0.764 m) of lithium metal rod pieces (0.5 in×0.5 in, 6 pieces) to give a total of 2.591 moles and 117 g (1.327 m) of methyl tert-butyl ether. To the dropping funnel was added 68.7 g (0.426 m) of hexamethyldisilazane and 21.0 g (0.2015 m) of styrene. The reactor was heated to 49.7° C. and the feed begun at a rate of about 1–2 drops per second. The reaction mixture gradually became copper-tinted, although the lithium particles remained mostly shiny. The reaction temperature was allowed to rise to near the boiling point of the solvent (57.6° C.) at the end of the addition and then allowed to drop off on its own. The yield of product versus post-addition time was monitored with the following results: 6 min, 86.2%; 14 min, 91.8%; 9 min, 93.3%; 34 min, 95.4% (ca 33 wt % of product in solution). Some crystals precipitated from solution at 16° C., but dilution of the product mixture to 26 wt % led to a stable product even as cold as −10° C.

Exemplary Run of Lithium Hexamethyldilazide Employing Lithium Dispersion (Solvent=Methyl tert-butyl ether & Heptane) (8551)

A weight of 7.10 g (1.02 m) of lithium metal powder containing 0.89% sodium, 85 ml heptane and 66.1 g (0.7498 m) of methyl tert-butyl ether was placed in a 500 ml flask equipped as described previously. A mix of 19.85 g (0.1905 m) of styrene and 68.5 g (0.4244 m) hexamethyldisilazane was added to the dropping funnel. Addition of the solution was begun at room temperature and was controlled at 33°–36° C. during the remainder of the addition. After an additional 3 hours of stirring, the reaction mixture (including excess lithium metal) was transferred to a filter funnel and filtered to give a very pale yellow solution (236.5 g), assay of the solution indicated a 96.8% yield (1.56 m/kg). The use of bulk metal in place of lithium powder, with methyl tert-butyl ether as a solvent, gave comparable results. (See 8802)

Preparation of Lithium t-Butyl-, trimethylsilyl Amide Using Bulk Lithium Metal (Solvent= THF) (8835)

Thirty-two pieces of lithium metal (2.412 moles) from a previous reaction were washed three times with 50 ml of THF and mixed in a reaction with 50.10 grams (0.3447 moles) of tert-butyl-trimethylsilylamine.

A weight of 136.1 g ( 1.887 m) of THF was placed in the dropping funnel and 100 ml of it drained into the reactor. Then, 17.4 g (0.1671 m) of styrene was mixed in with the THF in the dropping funnel and the solution fed slowly to the reactor contents at 40°–41° C. over a period of 27 minutes. The yield 6 min after the feed was 80.7%. Twenty-six minutes after the feed, the yield had not increased appreciably (82%). A weight of 216 grams of a yellow, hazy solution was obtained.

| PREPARATION OF LITHIUM HEXAMETHYLDISILAZIDE IN THF EMPLOYING BULK LITHIUM[a] | | | | | | | | | |
|---|---|---|---|---|---|---|---|---|---|
| | REAGENTS | | | | | CONDITIONS | | RESULTS | |
| | | | | | | | HMDS/Styrene | Conv. | |
| Exp. No | Lithium moles | HMDS moles | Li/HMDS mole ratio | Styrene moles | THF moles | Rx Temp °C. | Feed min | moles/ kg | Conv. % | Time[b] min |
| 8768 | 1.079 | 0.420 | 2.57 | 0.202 | 1.58 | 44–46 | 36 | 1.88[c] | 94.5 | 69 |
| 8772 | 1.179 | 0.515 | 2.29 | 0.251 | 2.52 | 33–47 | 41 | 1.59 | 92.6 | 188 |
| 8773 | 1.166 | 0.498 | 2.34 | 0.235 | 2.53 | 45–72 | 39 | 1.56 | 95.1 | 129 |
| 8776 | 0.791 | 0.432 | 1.83 | 0.211 | 2.53 | 57–73 | 53 | 1.45 | 94.0 | 113 |
| 8780 | 1.110 | 0.418 | 2.66 | 0.202 | 2.46 | 37–46 | 34 | 1.38 | 91.4 | 136 |
| 8781 | 2.302 | 0.532 | 4.33 | 0.238 | 2.75 | 37–41 | 34 | 1.44 | 93.6 | 120 |

[a]consecutive runs using metal from previous run plus added metal
[b]includes feed time
[c]product precipitates from solution

What is claimed is:

1. A process for quickly preparing easily separable solutions of lithium alkylamides, as exemplified by the formula $$(R_3M)_xNLi(R1)_y \cdot (LB)_z \qquad (I)$$

wherein M is silicon or carbon, R and $R^1$ are $C_1$-$C_8$ alkyl, cycloalkyl or alkylene groups, LB is a Lewis base, x and y are integers equaling 2, and z is greater than 1, comprising the steps of reacting lithium metal in bulk form with an alkylamine in mole ratios of metal to alkylamine ranging from 2 to 1 to 10 to 1 in a solvent selected from ethereal or mixed ethereal/hydrocarbon solvents in the presence of an electron carrier selected from the group consisting of conjugated dienes, vinyl aromatic and polycyclic aromatic compounds, under an inert atmosphere at elevated temperatures for 1 to 10 hours, cooling the product and separating the product solution from the unreacted lithium metal in the reactor.

2. The process of claim 1 in which the alkylamine is diisopropylamine, the solvent is a mixture of tetrahydrofuran and heptane, the electron carrier is styrene and the lithium metal to alkylamine ratio is 3 to 1.

3. The process of claim 1 in which the alkylamine is hexamethyldisilazane, the solvent is tetrahydrofuran, the electron carrier is styrene, the lithium metal to alkylamine ratio is 3 to 1, and the elevated temperature is the reflux temperature.

4. The process of claim 1 in which the bulk lithium metal pieces initially charged to the reactor are of a weight greater than 0.5 grams per piece.

5. The process of claim 1 wherein the separation of the product is carried out by decantation.

6. The process of claim 1 in which the alkylamine is hexamethyldisilazane, the solvent is methyl tert-butyl ether, the electron carrier is styrene, the lithium metal to alkylamine ratio is 3 to 1, and the elevated temperature is the reflux temperature.

7. A process for quickly preparing easily separable solutions of lithium alkylamide comprising the steps of reacting lithium metal in bulk form, with an alkylamine in mole ratios of metal to alkylamine ranging from 2 to 1 to 10 to 1 in a solvent selected from ethereal or ethereal/hydrocarbon solvents in the presence of an electron carrier selected from, the group consisting of conjugated dienes, vinyl aromatic and polycyclic aromatic compounds, under an inert atmosphere at elevated temperature for 1 to 10 hours, cooling the product and separating the product solution from the unreacted lithium metal in the reactor, adding additional solvent and sufficient lithium metal, electron carrier and alkylamine to the unreacted metal in the reactor to re-establish the mole ratio of lithium metal to alkylamine, and continuing the reaction, thereby forming further lithium alkylamide, and repeating these process steps a number of times.

8. The process of claim 10 wherein the number of repetitions of said reaction steps is at least three.

9. The process of claim 1 wherein the conjugated diene is isoprene.

10. The process of claim 7 wherein the conjugated diene is isoprene.

* * * * *